United States Patent
Bauerfeind

(10) Patent No.: US 11,555,259 B2
(45) Date of Patent: Jan. 17, 2023

(54) POLYMER COMPOSITIONS, FIBERS AND THREADS WITH PETROLATUM AND/OR OLEIC ACID-CONTAINING OILS

(71) Applicant: BAUERFEIND AG, Zeulenroda-Triebes (DE)

(72) Inventor: Hans B. Bauerfeind, Zeulenroda-Triebes (DE)

(73) Assignee: BAUERFEIND AG, Zeulenroda-Triebes (DE)

( * ) Notice: Subject to any disclaimer, the term of this patent is extended or adjusted under 35 U.S.C. 154(b) by 555 days.

(21) Appl. No.: 15/757,393

(22) PCT Filed: Sep. 9, 2016

(86) PCT No.: PCT/EP2016/071352
§ 371 (c)(1),
(2) Date: Mar. 5, 2018

(87) PCT Pub. No.: WO2017/042362
PCT Pub. Date: Mar. 16, 2017

(65) Prior Publication Data
US 2018/0258556 A1    Sep. 13, 2018

(30) Foreign Application Priority Data

Sep. 11, 2015 (DE) ............... 10 2015 217 382.8

(51) Int. Cl.
| | | |
|---|---|---|
| *D01F 1/10* | (2006.01) | |
| *D01F 2/02* | (2006.01) | |
| *D01F 6/62* | (2006.01) | |
| *A41B 1/08* | (2006.01) | |
| *A41B 9/00* | (2006.01) | |
| *A41B 11/00* | (2006.01) | |
| *A41D 1/04* | (2006.01) | |
| *A41D 1/08* | (2018.01) | |
| *A61F 13/00* | (2006.01) | |
| *A61F 13/08* | (2006.01) | |
| *A61L 15/22* | (2006.01) | |
| *A61L 15/44* | (2006.01) | |
| *D04H 1/08* | (2012.01) | |

(52) U.S. Cl.
CPC .......... *D01F 1/10* (2013.01); *A41B 1/08* (2013.01); *A41B 9/001* (2013.01); *A41B 11/00* (2013.01); *A41D 1/04* (2013.01); *A41D 1/08* (2013.01); *A61F 13/00012* (2013.01); *A61F 13/00017* (2013.01); *A61F 13/08* (2013.01); *A61L 15/225* (2013.01); *A61L 15/44* (2013.01); *D01F 2/02* (2013.01); *D01F 6/625* (2013.01); *D04H 1/08* (2013.01); *A61L 2300/418* (2013.01); *D10B 2201/22* (2013.01); *D10B 2201/24* (2013.01); *D10B 2331/02* (2013.01); *D10B 2331/04* (2013.01); *D10B 2401/12* (2013.01); *D10B 2501/021* (2013.01); *D10B 2501/04* (2013.01); *D10B 2509/02* (2013.01)

(58) Field of Classification Search
CPC .. D01F 1/10; D01F 2/02; D01F 6/625; D04H 1/08; D10B 2501/021; A41B 11/00; A61F 13/08; A61L 15/44
See application file for complete search history.

(56) References Cited

U.S. PATENT DOCUMENTS

| | | | |
|---|---|---|---|
| 3,150,049 A * | 9/1964 | Emory | A61Q 19/10 424/447 |
| 3,201,353 A * | 8/1965 | Corben | B01J 13/08 428/402.2 |
| 4,157,320 A | 6/1979 | Yankner et al. | |
| 5,766,746 A | 6/1998 | Kampl et al. | |
| 6,626,961 B1 * | 9/2003 | Everhart | A61K 8/0208 604/358 |
| 7,550,541 B2 | 6/2009 | Ohme et al. | |
| 2002/0128621 A1 * | 9/2002 | Kruchoski | A61K 8/92 604/385.01 |
| 2004/0116018 A1 * | 6/2004 | Fenwick | A61K 8/891 442/164 |
| 2008/0044580 A1 | 2/2008 | Marte et al. | |
| 2008/0268005 A1 * | 10/2008 | Falkowski | D06M 23/02 424/401 |
| 2010/0093888 A1 | 4/2010 | Endo et al. | |
| 2011/0045078 A1 | 2/2011 | Kolbe et al. | |
| 2013/0012093 A1 | 1/2013 | Bond et al. | |

(Continued)

FOREIGN PATENT DOCUMENTS

| | | |
|---|---|---|
| CA | 2 705 962 A1 | 12/2010 |
| CN | 1871958 A | 12/2006 |

(Continued)

OTHER PUBLICATIONS

Garti, Nissim Widlak, Neil R.. (2012). Cocoa Butter and Related Compounds—17.2 Shea Butter Composition. AOCS Press. Retrieved from https://app.knovel.com/hotlink/pdf/id:kt00A5QO85/cocoa-butter-related/saponifiable-fraction (Year: 2012).*

(Continued)

*Primary Examiner* — Larissa Rowe Emrich

(74) *Attorney, Agent, or Firm* — Pearne & Gordon LLP

(57) ABSTRACT

This invention relates to a polymer composition containing at least one polymer and at least one agent, formed bodies having such a polymer composition, the use of the formed bodies and polymer compositions, and corresponding threads, nonwoven materials, clothing articles, and medical aids.

22 Claims, No Drawings

(56) References Cited

U.S. PATENT DOCUMENTS

2013/0053479 A1* 2/2013 Bond .................. C08K 5/0008
524/57
2015/0007850 A1 1/2015 Molenda et al.

FOREIGN PATENT DOCUMENTS

| CN | 100420398 C | 9/2008 |
| CN | 103547619 A | 1/2014 |
| DE | 29 10 893 A1 | 10/1979 |
| DE | 100-37 983 A1 | 4/2001 |
| DE | 100 07 794 A1 | 6/2001 |
| DE | 10 2006 019 820 A1 | 11/2006 |
| DE | 10 2007 054 702 A1 | 5/2009 |
| DE | 10 2008 037 633 A1 | 2/2010 |
| DE | 10 2013 225 848 A1 | 6/2015 |
| EP | 1 445 282 A1 | 8/2004 |
| EP | 1 698 661 A1 | 9/2006 |
| GB | 17403 A | 8/1909 |
| JP | 2006-345997 A | 12/2006 |
| JP | 2010-116656 A | 5/2010 |
| JP | 2012-097399 A | 5/2012 |
| JP | 2012097399 A * | 5/2012 |
| JP | 2013-144855 A | 7/2013 |
| WO | 01/40364 A1 | 6/2001 |
| WO | 2005/061603 A1 | 7/2005 |
| WO | 2006/007753 A1 | 1/2006 |
| WO | 2012/162083 A1 | 11/2012 |
| WO | 2012/162130 A1 | 11/2012 |
| WO | 2015/139965 A1 | 9/2015 |

OTHER PUBLICATIONS

"JP2012097399_Machine Translation" is a machine translation of JP-2012097399-A. (Year: 2012).*

Chinese Office Action dated Nov. 29, 2019 for corresponding Chinese Application No. 201680050805.4 and English translation.

English translation of Written Opinion dated Nov. 25, 2016 for corresponding International Application No. PCT/EP2016/071352.

International Preliminary Report on Patentability dated Mar. 13, 2018 for corresponding International Application No. PCT/EP2016/071352.

Russian Office Action dated Dec. 4, 2018 for corresponding Russian Application No. 201811271605.

Japanese Office Action dated Jun. 25, 2019 for corresponding Japanese Application No. 2018-512894 and English translation.

Westphal et al., "Medical compression stockings on the skin moisture in patients with chronic venous disease", Vasa (2019); https://doi.org/10.1024/0301-1526/a000812.

Bauerfeind, "Evidence of improving skin properties through use of medical compression stockings with integrated skin care substances", 2017.

International Search Report dated Nov. 25, 2016 for corresponding International Application No. PCT/EP2016/071352.

Written Opinion dated Nov. 25, 2016 for corresponding International Application No. PCT/EP2016/071352.

* cited by examiner

POLYMER COMPOSITIONS, FIBERS AND THREADS WITH PETROLATUM AND/OR OLEIC ACID-CONTAINING OILS

This invention relates to a polymer composition containing a polymer and at least one agent, formed bodies having such a polymer composition, the use of the formed bodies and polymer compositions, and corresponding threads, nonwoven fabrics, clothing articles, sports aids, and medical aids.

Polymer compositions, which are "functionalized" by additives, are known. For example, U.S. Pat. No. 5,766,746 describes cellulose fibers that contain a flame-resistant component DE 100 37 983 A1 describes polymer compositions having an alkaloid content and DE 100 07 794 A1 describes polymer compositions having a material from marine plants or animals.

Such polymer compositions are further processed into threads, textile surfaces, and clothing articles.

The addition of additives for functionalizing polymer fibers frequently leads to problems of maintaining necessary properties, particularly mechanical strengths loop strength, fiber elongation, chafing properties and dyeability, when the fibers are used.

However, there is a constant demand for functional fibers with specific additives and for clothing articles, sports aids, or medical aids produced from these, hence it is important to provide such fibers in which the difficulties described are overcome so that functionalized fibers and textile surfaces can fulfill the corresponding requirements for the clothing articles, sports aids, or medical aids produced from them.

Additives of particular relevance for the market are additives having an effect on the body of the wearer of the clothing articles, sports aids, or medical aids produced from the polymer compositions.

Structures known to date contain only low concentrations of these substances. These substances are applied to the carrier matrix by impregnation or coating. This leads to low washing resistance, for example; hence such substances must be routinely re-supplied in order for their mode of action to be maintained.

The technical problem addressed by this invention is therefore that of providing a polymer composition that contains a suitable additive, wherein the formed bodies made from the polymer composition still exhibit good stability and processability.

In the case of clothing articles and medical aids resting in close contact with the skin (e.g., bandages and compression stockings), regulation of skin moisture plays a role in wearing comfort; dehydration of the skin should be prevented in particular. Also, such textile surfaces should not lead to skin dehydration and skin irritations, nor aggravate existing skin conditions such as atopic dermatitis or neurodermatitis. Also, itching or pain associated with such skin conditions should be at least reduced.

The underlying technical problem of this invention is also the provision of clothing articles and medical aids, and the source material thereof, that are improved in this respect in particular.

This invention solves its underlying technical problem with the subject matter of the independent claims.

This invention solves its underlying technical problem in particular with a polymer composition containing a polymer and at least one agent selected from the group consisting of petrolatum, an oil or a fat, wherein the oil or the fat contains at least 25 wt % oleic acid, a non-saponifiable lipid from an oil, wherein the oil contains at least 25 wt % oleic acid, and mixtures thereof.

This invention solves its underlying technical problem in particular with a polymer composition containing a polymer and at least one agent selected from the group consisting of petrolatum, an oil, wherein the oil contains at least 25 wt % oleic acid, and mixtures thereof.

This invention also solves its underlying technical problem in particular with a thread or a textile surface containing fibers, wherein the fibers comprise a polymer composition containing a polymer and at least one agent selected from the group consisting of petrolatum, an oil or a fat, wherein the oil or the fat contains at least 25 wt % oleic acid, a non-saponifiable lipid from an oil, wherein the oil contains at least 25 wt % oleic acid, and mixtures thereof.

This invention also solves its underlying technical problem in particular with a thread or a textile surface containing fibers, wherein the fibers comprise a polymer composition containing a polymer and at least one agent selected from the group consisting of petrolatum, an oil, wherein the oil contains at least 25 wt % oleic acid, a non-saponifiable lipid from an oil, wherein the oil contains at least 25 wt % oleic acid, and mixtures thereof.

This invention also solves its underlying technical problem in particular with a thread or a textile surface containing fibers, wherein the fibers comprise a polymer composition containing a polymer and at least one agent selected from the group consisting of petrolatum, an oil, wherein the oil contains at least 25 wt % oleic acid, and mixtures thereof.

This invention also solves its underlying technical problem in particular with a thread containing fibers, wherein the fibers comprise a polymer composition containing a polymer and at least one agent selected from the group consisting of petrolatum, an oil, wherein the oil contains at least 25 wt % oleic acid, and mixtures thereof.

This invention also solves its underlying technical problem in particular with a textile surface containing fibers, wherein the fibers comprise a polymer composition containing a polymer and at least one agent selected from the group consisting of petrolatum, an oil, wherein the oil contains at least 25 wt % oleic acid, and mixtures thereof.

This invention preferably solves its underlying technical problem with a polymer composition containing a polymer and petrolatum.

This invention preferable solves its underlying technical problem in particular with thread or a textile surface containing fibers, wherein the fibers comprise a polymer composition containing a polymer and petrolatum.

Petrolatum is a paraffin mixture that is formed in particular from C12 to C85 hydrocarbons, in particular with a predominant fraction of crystalline and liquid saturated hydrocarbons with more than 25 carbon atoms. Petrolatum has a melting point of between 25° C. and 60° C., in particular 36° C. to 60° C., preferably 38° C. and 60° C. Petrolatum was discovered in 1859. Petrolatum is a semisolid paraffin at room temperature or body temperature.

Petrolatum is known as a "penetration enhancer". It enhances the penetration of the stratum corneum with lipophilic substances. In the stratum corneum, petrolatum brings about a configuration change in the orthorhombic order of intercellular lipids and counteracts water loss. In this process, petrolatum causes a swelling in the embedded corneocytes due to water retention. The intracellular path is considerably less significant.

Typical penetration enhancing substances such as amines, alcohols, Azone, etc. lead to the disruption of the stratum corneum in order to provide the added agent (e.g., medicine) access to the dermis.

It has now been found that petrolatum, also in a polymer composition, is advantageously suited for skin-friendly use as a penetration enhancer, as it has biomimetic properties and, like a physiological lipid, interacts with the intracellular lipids of the stratum corneum.

In an advantageous manner, petrolatum is furthermore capable of effecting the restoration of the barrier function after damage to the stratum corneum. Although petrolatum is not chemically related to skin lipids, in the stratum corneum the mixture of saturated straight-chain and branched hydrocarbons of petrolatum can reduce or even eliminate the disorder in the zone of the intercellular lipids.

Petrolatum also has an advantageous spreading behavior.

It has now been found that these properties of petrolatum can also be exploited in polymer compositions and fibers formed therefrom, and that threads, textile surfaces, clothing articles, sports aids, or medical aids containing these fibers can also be exploited.

Hence the at least one agent is preferably petrolatum.

Alternatively, this invention solves its underlying technical problem with a polymer composition containing a polymer and an oil, wherein the oil contains at least 25 wt % oleic acid.

Alternatively, this invention also solves its underlying technical problem with a thread or a textile surface containing fibers, wherein the fibers comprise a polymer composition containing a polymer and an oil, wherein the oil contains at least 25 wt % oleic acid.

Surprisingly, it was found that oils with a high oleic acid fraction are also suitable as penetration enhancers, also as an agent in a polymer composition.

Preference is given to a polymer composition containing a polymer and a mixture of petrolatum and an oil, wherein the oil contains at least 25 wt % oleic acid.

Hence the invention also preferably relates to a thread according to the invention or to a textile surface according to the invention, in which the polymer composition contains petrolatum and the oil that contains at least 25 wt % oleic acid.

The at least one agent preferably serves to enhance penetration through the skin.

Preference is thus given to a thread according to the invention or to a textile surface according to the invention, in which the at least one agent serves to enhance penetration through the skin.

The at least one agent, in particular the petrolatum, is preferably an occlusive agent. Petrolatum is advantageously suited as an occlusive agent. Shea butter, particularly in combination with petrolatum, can also be used as an occlusive agent.

Hence preference is given to a thread according to the invention or to a textile surface according to the invention, in which the at least one agent is an occlusive agent.

In connection with this invention, occlusion is understood to mean the prevention or reduction of water loss via the skin to the surroundings, for example to a textile padding.

In addition to other important functions, the human skin protects against adverse influences from the environment. In order to maintain its protective function, it is of considerable importance to prevent the loss of water from the deeper layers of skin.

The structure of human skin is divided into three components, namely the epidermis, the dermis, and the subcutis.

The outer layers of the stratum corneum of the epidermis, with their keratin filaments, play a special role in terms of the water content of the skin. The keratin fibrous scaffold can thus hold considerable quantities of water. The target and action point of the external occlusive effect of a given substance is the epidermis. The main effect, namely preventing a loss of water from the stratum corneum (transepidermal water loss (TEWL)), is brought about by applying such a substance to the skin surface. These substances result in the formation of a film, which presents moisture loss. In the case of outer occlusion, water is thus able to move up from the deeper layers und fill the keratin fibrous scaffold of the outer skin layer with moisture. The stratum corneum thus protects against dehydration. The elasticity and suppleness of the skin are maintained and the skin maintains its physiological equilibrium for protection against harmful external influences, for example. This occlusive mode of action of an agent is also designated as external occlusion.

Inner occlusion designates a change in the skin lipid configuration in the stratum corneum. In the hexagonal configuration, the hydrocarbon chains of the lipids can rotate freely about their axes. This phase of "loose packing" results in a more porous, in other words permeable structure and facilitates an undesired water loss under stress in the stratum corneum with corresponding adverse consequences such as dryness of the skin. Under the effect of certain agents, a denser orthorhombic packing of the lipids is generated in the case of inner occlusion. This arrangement leads to a firm structure. By the "orthorhombic packing" of the lipids, such a molecular action results in considerably less permeability of the skin barrier and thus significantly reduces water loss from the stratum corneum. As a preferred agent, petrolatum advantageously acts as a facilitator in the inner occlusion process.

The at least one agent, in particular petrolatum, is preferably an inner occlusive agent.

The at least one agent is preferably petrolatum. The agent is preferably petrolatum.

The agent is preferably a petrolatum according to CAS number 8009-03-8.

The petrolatum is preferably petrolatum USP, in other words a petrolatum that fulfills the USP (US Pharmacopeial Convention) requirements ("USP verified").

The petrolatum preferably contains at most 20 wt % saturated straight chain hydrocarbon with 20 to 45 carbon atoms. The petrolatum preferably contains at least 20 wt % and at most 25 wt % saturated straight chain hydrocarbons with 30 to 90 carbon atoms. The petrolatum preferably contains at least 40 wt % saturated straight chain hydrocarbons with 10 to 50 carbon atoms. Such kinds of petrolatum advantageously turn out to be less greasy and spread favorably under the effect of other agents, such as dicaprylyl carbonate, issuing from a fiber formed from the polymer composition according to the invention, in the skin zone.

The polymer composition, the thread, or the textile surface preferably additionally contains at least one agent, wherein said agent can be an occlusive agent, in particular an internal occlusive agent or an external occlusive agent, a moisturizing agent, or a pain-reducing or itch-reducing agent, or mixtures thereof. The additional agent is preferably an occlusive agent, is particular an internal occlusive agent or as external occlusive agent.

In connection with this invention, occlusion is understood to mean the prevention or reduction of water loss via the skin to the surroundings, for example a textile surface.

Hence preference is also given to a thread according to the invention or to a textile surface according to the invention, in which the polymer composition additionally contains an agent selected from the group consisting of dicaprylyl carbonate, cetyl isononanoate, cetearyl isononanoate, isopropyl isostearate, isostearyl isostearate, isopropyl palmitate, shea butter, and mixtures thereof.

Hence preference is also given to a thread according to the invention or to a textile surface according to the invention, in which the polymer composition additionally contains an agent selected from the group consisting of cetyl isononanoate, cetearyl isononanoate, dicaprylyl carbonate, isopropyl isostearate, isostearyl isostearate, isopropyl palmitate, and mixtures thereof.

Cetyl isononanoate has the CAS number 84878-33-1. Cetearyl isononanoate has the CAS number 11937-03-02.

Hence preference is also given to a thread according to the invention or to a textile surface according to the invention, in which the polymer composition additionally contains cetyl isononanoate.

Hence preference is also given to a thread according to the invention or to a textile surface according to the invention, in which the polymer composition additionally contains cetearyl isononanoate.

Hence preference is also given to a thread according to the invention or to a textile surface according to the invention, in which the polymer composition additionally contains dicaprylyl carbonate.

Hence preference is also given to a thread according to the invention or to a textile surface according to the invention, in which the polymer composition additionally contains isopropyl isostearate.

Hence preference is also given to a thread according to the invention or to a textile surface according to the invention, in which the polymer composition additionally contains isostearyl isostearate.

Hence preference is also given to a thread according to the invention or to a textile surface according to the invention, in which the polymer composition additionally contains isopropyl palmitate.

Hence preference is also given to a thread according to the invention or to a textile surface according to the invention, in which the polymer composition additionally contains shea butter.

Preference is given to a polymer composition containing a polymer, petrolatum (PET) and cetyl isononanoate (CEIN).

Preference is given to a polymer composition containing a polymer and a mixture of petrolatum (PET) and cetyl isononanoate (CEIN).

An alternative is a polymer composition containing a polymer and a mixture of petrolatum (PET) and cetearyl isononanoate. An alternative is a polymer composition containing a polymer and a mixture of petrolatum (PET) and dicaprylyl carbonate (DICA). Dicaprylyl carbonate constitutes the favorable functional partner for the lipophilic constituent PET and prevents the "greasy skin feeling" thereof.

An alternative is a polymer composition containing a polymer and a mixture of petrolatum and a fatty acid derivative, in particular isopropyl isostearate (IPIS) or isostearyl isostearate (ISIS), which are known as internal occlusive agents.

Preference is given to a polymer composition containing a polymer and a mixture of petrolatum and isopropyl isostearate. Alternatively, preference is given to a polymer composition containing a polymer and a mixture of petrolatum and isostearyl isostearate.

As a penetration enhancer, petrolatum supports the effect of ISIS and IPIS as internal occlusive agents. Furthermore, petrolatum itself is an agent that generates as occlusion.

Hence preference is also given to a thread according to the invention or to a textile surface according to the invention in which the polymer composition contains petrolatum and another agent selected from the group consisting of cetyl isononanoate, dicaprylyl carbonate, isopropyl isostearate, isostearyl isostearate, and mixtures thereof.

Hence preference is also given to a thread according to the invention or to a textile surface according to the invention in which the polymer composition contains petrolatum and another agent selected from the group consisting of dicaprylyl carbonate, cetyl isononanoate, cetearyl isononanoate, isopropyl isostearate, isostearyl isostearate, isopropyl palmitate, and mixtures thereof.

Preference is given to a polymer composition containing a polymer and a mixture of petrolatum and at least one oil and/or a mixture of petrolatum, and at least one fat.

Preference is given to a polymer composition containing a polymer and a mixture of petrolatum and an oil and/or a mixture of petrolatum and a fat.

Preference is given to a polymer composition containing a polymer and a mixture of petrolatum and a fat. The fat is preferably a vegetable fat.

The fat preferably contains oleic acid. The fat preferably contains at least 25 wt % oleic acid. The fat preferably contains at least 35 wt % oleic acid. The fat preferably contains at least 40 wt % oleic acid. The fat preferably contains palmitic acid. The fat preferably contains at least 2 wt % palmitic acid. The fat preferably contains stearic acid. The fat preferably contains at least 30% stearic acid. The fat preferably contains oleic acid, palmitic acid, and stearic acid.

The fat is preferable shea butter. Preference is thus given to a polymer composition containing a polymer and a mixture of petrolatum and shea butter.

Shea batter is extracted from the karité nut of the karité tree. The karité tree, also known as the shea tree, shi tree or African butter tree (*Vitellaria paradoxa*, syn. *Butyrospermum parkii*), is the only species in the genus *Vitellaria* in the Sapotaceae family. The unique feature of shea butter is the high fraction of non-saponifiable constituents (ca. 75% triterpenes, in addition to oleic acid, triterpene alcohols, vitamin E, beta-carotene and allantoin). Shea butter contains chiefly long chain unsaturated fatty acids. The main constituents are 40-55% oleic acid, 35-45% stearic acid, 3-8% linoleic acid and 3-7% palmitic acid.

The triterpenes contained in shea butter advantageously have an anti-inflammatory action. For example, a mixture of petrolatum USP and shea butter is marketed as Shea XP™ by the firm Sonneborn LLC (USA). The triterpenes of shea butter can act synergistically with the petrolatum for improving skin moisture and reducing tansepidermal water loss.

Preference is given to a polymer composition containing a polymer, petrolatum (PET), shea butter and cetyl isononanoate (CEIN).

Alternatively, this invention solves its underlying technical problem with a polymer composition containing a polymer and shea butter.

Preference is given to a polymer composition containing a polymer and a mixture of petrolatum and an oil. The oil preferably contains oleic acid. The oil preferably contains at least 25 wt % oleic acid. The oil preferably contains at least 35 wt % oleic acid. The oil preferable contains at least 40 wt % oleic acid. The oil preferably contains palmitic acid. The oil preferably contains at least 20 wt % palmitic acid. The oil preferably contains stearic acid. The oil preferably contains at least 5 wt % stearic acid. The oil preferably contains oleic acid, palmitic acid and stearic acid.

Alternatively, this invention solves its underlying technical problem with a polymer composition containing a polymer and an oil, wherein the oil contains at least 25 wt % oleic acid.

Alternatively, this invention also solves its underlying technical problem with a thread or a textile surface containing fibers, wherein the fibers comprise a polymer composition containing a polymer and an oil, wherein the oil contains at least 25 wt % oleic acid.

Hence preference is also given to a thread according to the invention or to a textile surface according to the invention, wherein the oil contains at least 35 wt % oleic acid, at least 20 wt % palmitic acid, at least 3 wt % palmitoleic acid, at least 5 wt % linoleic acid, at least 5 wt % stearic diacid, and at least 0.5 w % cis-9-octadecenoic acid.

The oil can be a synthetic or a natural oil.

The oil preferably contains at least 35 wt % oleic acid. The oil preferably contains at least 40 wt % oleic acid.

The oil preferably contains at least 35 wt % oleic acid and at least 20 wt % palmitic acid.

The oil preferably contains at least 35 wt % oleic acid, at least 20 wt % palmitic acid, and at least 5 wt % stearic diacid.

The oil preferably contains at least 35 wt % oleic acid, and in addition palmitic acid, linoleic acid and stearic diacid.

The oil preferably contains at least 35 wt % oleic acid, and in addition palmitic acid, palmitoleic acid, linoleic acid and stearic diacid.

The oil preferably contains at least 35 wt % oleic acid, and in addition palmitic acid, palmitoleic acid, linoleic acid, stearic diacid and cis-9-octadecenoic acid.

The oil preferably contains at least 35 wt % oleic acid, at least 20 wt % palmitic acid, at least 3 wt % palmitoleic acid, at least 5 wt % linoleic acid, at least 5 wt % stearic diacid and at least 0.5 wt % cis-9-octadecenoic acid.

Hence preference is also given to a thread according to the invention or to a textile surface according to the invention in which the oil is marula oil, olive oil and/or rapeseed oil or a non-saponifiable lipid of rapeseed oil.

Hence preference is also given to a thread according to the invention or to a textile surface according to the invention in which the oil is marula oil, olive oil, and/or rapeseed oil. The oils can be contained individually or in mixtures.

The oil is preferably rapeseed oil, in particular canola oil. The oil is preferably canola oil. Canola oil is the oil of a newly-developed rape variety, which is low in erucic acid and glucosinolate. It was found that canola oil is very well suited for skin care and/or for preventing the skin from drying out.

Alternatively, the oil is marula oil. Marula oil is the oil that is extracted from the seeds of the fruit of the marula tree (Sclerocarya birreci). It advantageously contains up to or more than 70 wt % oleic acid.

The polymer composition preferably contains petrolatum and rapeseed oil, in particular canola oil.

The polymer composition preferably contains petrolatum and marula oil.

Alternatively, the oil can be olive oil.

Also preferred is a thread according to the invention or a textile surface according to the invention, in which the polymer composition contains non-saponifiable lipids. The non-saponifiable lipids can be used alternatively to the oil or in addition to the oil. The non-saponifiable lipids preferably originate from an oil, wherein the oil contains at least 25 wt % oleic-acid. The non-saponifiable lipids preferably originate from rapeseed oil, olive oil, and/or marula oil, in particular rapeseed oil. The non-saponifiable lipids preferably originate from canola oil.

Non-saponifiable lipids are either fatty acids or derivatives thereof, or isoprene derivatives or triterpenes. They can be extracted from, for example, canola oil as the easily produced fraction and they are surprisingly also very good for skin care and/or for preventing the skin from drying out.

Hence preference is also given to a thread according to the invention or to a textile surface according to the invention, wherein the polymer composition contains canola-oil and/or non-saponifiable lipids from canola oil.

Hence preference is also given to a thread according to the invention or to a textile surface according to the invention, wherein the polymer composition contains petrolatum, shea butter, and an oil that contains at least 25 wt % oleic acid.

Also preferred is a thread according to the invention or a textile surface according to the invention, in which the polymer composition contains petrolatum, shea butter and canola oil, and/or non-saponifiable lipids from canola oil.

Also preferred is a thread according to the invention or a textile surface according to the invention, in which the polymer composition contains petrolatum, shea butter, and an oil selected from the group consisting of canola oil, marula oil, and olive oil.

Also preferred is a thread according to the invention or a textile surface according to the invention, in which the polymer composition contains shea butter and an oil that contains at least 25 wt % oleic acid.

Also preferred is a thread according to the invention or a textile surface according to the invention, in which the polymer composition contains shea butter and an oil selected from the group consisting of canola oil, marula oil, and olive oil.

Hence preference is also given to a thread according to the invention or to a textile surface according to the invention, in which the polymer composition contains oil, which contains at least 25 wt % oleic acid, and another agent selected from the group consisting of dicaprylyl carbonate, cetyl isononanoate, isopropyl isostearate, isostearyl isostearate, and mixtures thereof.

Hence preference is also given to a thread according to the invention or to a textile surface according to the invention, in which the polymer composition contains oil, which contains at least 25 wt % oleic acid, and another agent selected from the group consisting of dicaprylyl carbonate, cetyl isononanoate, cetearyl isononanoate, isopropyl isostearate, isostearyl isostearate, isopropyl palmitate, and mixtures thereof.

Hence preference is also given to a thread according to the invention or to a textile surface according to the invention, in which the polymer composition contains marula oil, olive oil, and/or rapeseed oil and another agent selected from the group consisting of dicaprylyl carbonate, cetyl isononanoate, isopropyl isostearate, isostearyl isostearate, and mixtures thereof.

Hence preference is also given to a thread according to the invention or to a textile surface according to the invention, in which the polymer composition contains marula oil and another agent selected from the group consisting of dicaprylyl carbonate, cetyl isononanoate, isopropyl isostearate, isostearyl isostearate, and mixtures thereof.

Hence preference is also given to a thread according to the invention or to a textile surface according to the invention, in which the polymer composition contains marula oil, olive oil, and/or rapeseed oil and another agent selected from the group consisting of dicaprylyl carbonate, cetyl isononanoate, cetearyl isononanoate, isopropyl isostearate, isostearyl isostearate, isopropyl palmitate, and mixtures thereof.

Hence preference is also given to a thread according to the invention or to a textile surface according to the invention, in which the polymer composition contains marula oil and another agent selected from the group consisting of dicaprylyl carbonate, cetyl isononanoate, cetearyl isononanoate, isopropyl isostearate, isostearyl isostearate, isopropyl palmitate, and mixtures thereof.

Hence preference is also given to a thread according to the invention or to a textile surface according to the invention, in which the polymer composition contains a) petrolatum and b) oil that contains at least 25 wt % oleic acid.

Hence preference is also given to a thread according to the invention or to a textile surface according to the invention, in which the polymer composition contains a) petrolatum and b) marula oil, olive oil and/or rapeseed oil, in particular canola oil.

Hence preference is also given to a thread according to the invention or to a textile surface according to the invention, in which the polymer composition contains petrolatum and marula oil.

Hence preference is also given to a thread according to the invention or to a textile surface according to the invention, in which the polymer composition contains a) petrolatum, b) oil that contains at least 25 wt % oleic acid, and c) another agent selected from the group consisting of dicaprylyl carbonate, cetyl isononanoate, isopropyl isostearate, isostearyl isostearate, and mixtures thereof.

Hence preference is also given to a thread according to the invention or to a textile surface according to the invention, in which the polymer composition contains a) petrolatum, b) marula oil, olive oil and/or rapeseed oil and c) another agent selected from the group consisting of dicaprylyl carbonate, cetyl isononanoate, isopropyl isostearate, isostearyl isostearate, and mixtures thereof.

Hence preference is also given to a thread according to the invention or to a textile surface according to the invention, in which the polymer composition contains petrolatum, marula oil and another agent selected from the group consisting of dicaprylyl carbonate, cetyl isononanoate, isopropyl isostearate, isostearyl isostearate, and mixtures thereof.

Hence preference is also given to a thread according to the invention or to a textile surface according to the invention, in which the polymer composition contains a) petrolatum, b) oil that contains at least 25 wt % oleic acid and c) another agent selected from the group consisting of dicaprylyl carbonate, cetyl isononanoate, cetearyl isononanoate, isopropyl isostearate, isostearyl isostearate, isopropyl palmitate, and mixtures thereof.

Hence preference is also given to a thread according to the invention or to a textile surface according to the invention, in which the polymer composition contains a) petrolatum, b) shea butter and c) another agent selected from the group consisting of dicaprylyl carbonate, cetyl isononanoate, cetearyl isononanoate, isopropyl cetearyl isononanoate, isopropyl isostearate, isostearyl isostearate, isopropyl palmitate, and mixtures thereof.

Hence preference is also given to a thread according to the invention or to a textile surface according to the invention, in which the polymer composition contains a) petrolatum, b) marula oil, olive oil and/or rapeseed oil, and c) another agent selected from the group consisting of dicaprylyl carbonate, cetyl isononanoate, cetearyl isononanoate, isopropyl isostearate, isostearyl isostearate, isopropyl palmitate, and mixtures thereof.

Hence preference is also given to a thread according to the invention or to a textile surface according to the invention, in which the polymer composition contains petrolatum, marula oil, and another agent selected from the group consisting of dicaprylyl carbonate, cetyl isononanoate, cetearyl isononanoate, isopropyl isostearate, isostearyl isostearate, isopropyl palmitate, and mixtures thereof.

The aforementioned oils and also fats are suitable partners for petrolatum in a preferred lipophilic mixture for adding to fibers, in particular fibers made of biopolymers, in particular cellulose fibers. After they are processed into textiles and medical textiles and after they are delivered to the stratum corneum, they hydrate and reduce the roughness of the skin of the wearer, and act continuously for a period up to 28 days and longer. The efficacy over such a time period is particularly advantageous in the case of medical aids such as bandages and compression and support stockings, as the latter are often worn permanently, i.e. over a lengthy period of time.

According to the invention, the polymer composition therefore contains, in addition to the polymer, at least one agent, wherein the agent can be petrolatum, and/or an oil, wherein the oil contains at least 25 wt % oleic acid. Obviously the presence of these agents and of mixtures of these agents is therefore also encompassed by the invention.

Surprisingly, if was found that such agents can be introduced in a polymer composition and as additives therein; exert their effect, in particularly directly, on the underlying skin if the polymer composition is in contact with the skin in the form of corresponding products such as clothing articles and medical aids. In an advantageous manner, these agents are in particular capable of preventing dehydration of the skin. The agents can also be used to enable other agents to penetrate the skin.

It was found that in particular polymer compositions made of biopolymers, for example cellulose, can be loaded especially well with petrolatum and/or with an aforementioned oil or fat or an aforementioned non-saponifiable lipid, specifically in weight percentages of in particular up to 25% and more for petrolatum and in particular up to 35% and more for the oils, based on cellulose. For example, very good results have been obtained with weight percentages of up to 23% in particular for petrolatum and up to 11% in particular for the oils, based on cellulose.

The polymer composition preferably contains the petrolatum in a proportion of at least 1 wt % (based on the total weight of the polymer composition).

The polymer composition preferably contains the petrolatum in a proportion of at least 5 wt % (based on the total weight of the polymer composition).

The polymer composition preferably contains the petrolatum in a proportion of at least 10 wt % (based on the total weight of the polymer composition).

The polymer composition preferably contains the petrolatum in a proportion of at least 1 wt % and at most 40 wt % in particular at most 35 wt % (based on the total weight of the polymer composition). The polymer composition preferably contains the petrolatum in a proportion of at most 40 wt %, in particular at most 35 wt % (based on the total weight of the polymer composition).

The polymer composition preferably contains the petrolatum in a proportion of at least 1 wt % and at most 30 wt % in particular at most 25 wt % (based on the total weight of the polymer composition). The polymer composition preferably contains the petrolatum in a proportion of at most 30 wt %, in particular at most 25 wt % (based on the total weight of the polymer composition).

The polymer composition preferably contains the petrolatum in a proportion of at least 1 wt % and at most 23 wt % (based on the total weight of the polymer composition). The polymer composition preferably contains the petrolatum in a proportion of at most 23 wt %, (based on the total weight of the polymer composition).

The polymer composition preferably contains the oil in a proportion of at least 1 wt % (based, on the total weight of the polymer composition).

The polymer composition preferably contains the oil in a proportion of at least 5 wt % (based on the total weight of the polymer composition).

The polymer composition preferably contains the oil in a proportion of at least 1 wt % and at most 45 wt %, in particular at most 40 wt % (based on the total weight of the polymer composition). The polymer composition preferably contains the oil in a proportion of at most 45 wt %, in particular at most 40 wt % (based on the total weight of the polymer composition).

The polymer composition preferably contains the oil in a proportion of at least 1 wt % and at most 35 wt %, in particular at most 20 wt % (based on the total weight of the polymer composition). The polymer composition preferably contains the oil in a proportion of at most 35 wt %, in particular at most 20 wt % (based on the total weight of the polymer composition).

The polymer composition preferably contains the oil in a proportion of at least 1 wt % and at most 15 wt %, in particular at most 12 wt % (based on the total weight of the polymer composition). The polymer composition preferably contains the oil in a proportion of at most 15 wt %, in particular at most 12 wt % (based on the total weight of the polymer composition).

The polymer composition preferably contains the oil in a proportion of at least 1 wt % and at most 11 wt % (based on the total weight of the polymer composition). The polymer composition preferably contains the oil in a proportion of at most 11 wt % (based on the total weight of the polymer composition).

Without being bound by theory, in particular the preferred copolymers (e.g., cellulose) are capable of forming cavities that serve as loading zones for the agents. In an advantageous manner, a special production technique is thus unnecessary for the biopolymers and the fibers produced therefrom.

Surprisingly, it could also be confirmed that as a group, the agents according to the invention contained in the polymer composition as additives have good stability during the application period and are thus able to exert their effect throughout this period.

It has furthermore surprisingly been found that the polymer composition according to the invention, in particular if they contain biopolymers, in particular if they contain cellulose or are cellulose based, give rise to fibers that, despite the addition of at least one of the additives according to the invention, show the same outstanding properties as pure fibers, in particular cellulose fibers, in terms of their fineness, tear strength, tear strength variation, elongation, wet expansion, tear strength as related to fineness, wet tear strength as related to fineness, loop tear strength as related to fineness, wet chafing variation, and wet moduli.

Nevertheless these fibers simultaneously showed the positive properties imparted by the at least one additive.

The fibers are preferably produced from a spinning solution. In spite of the addition of at least one additive according to the invention, it was surprisingly found a spinning solution does not undergo any degradation, in particular if it contains cellulose, and more particularly if the spinning solution is made from cellulose, N-methylmorpholine-N-oxide (NMMNO), and water as main constituents.

Suitable production processes are known from DE 10 2007 054 702 A1, in particular for polymer compositions that contain cellulose or modified cellulose, and in particular in the form of formed bodies.

The polymer composition can contain polymers as they are typically used for the production of fibers, filaments, threads, nonwoven materials, clothing articles, and medical aids such as bandages and compression stockings.

The polymer is preferably a biopolymer, particularly preferably a technical biopolymer.

In a preferred embodiment, the polymer is selected from the group consisting cellulose, modified cellulose, polyamide, polyacrylic, polyester, polyurethane, polyethylene, polypropylene, modifications thereof and mixtures thereof. In a preferred embodiment, the polymer is selected from the group consisting of cellulose, modified cellulose, polyamide, polyacrylic, polyester, modifications thereof and mixtures thereof.

In a preferred embodiment, the polymer is selected from the group consisting of cellulose, modified cellulose, viscose, polylactides, modifications thereof, derivatives thereof, and mixtures thereof.

In a preferred embodiment, the polymer is cellulose, modified cellulose, viscose, or polylactide. In a preferred embodiment, the polymer is cellulose or polylactide.

In an alternative embodiment, the polymer is a starch polymer.

In a preferred embodiment, the polymer is biodegradable. The biodegradable polymer is preferably selected form the group consisting of cellulose, modified cellulose, latex, protein of vegetable or animal origin, and mixtures thereof. Polycondensation and polymerization polymers, polyurethanes, polyesters, polyacrylics, and mixtures of these materials may also be used.

However, in an alternative embodiment provision can also be made such that the polymer composition according to the invention also contains non-biodegradable polymers. Examples of such polymers are polyamides, aromatic polyamides, in particular aramides, polyacrylonitrile, polyester, or polyvinyl alcohols.

In a preferred embodiment, the polymer is cellulose, modified cellulose, or modifications thereof and mixtures thereof. In a preferred embodiment the polymer is cellulose or modified cellulose.

Cellulose is a polymer forming a hydrophilic network, the supramolecular structures of which are stabilized both in solution and in a solid via likewise hydrophilic hydrogen bonds. In contrast, the agents that are used in this invention are selected from the group consisting of internal occlusive agents, external occlusive agents, and moisturizing agents, which are instead nonpolar, lipophilic organic compounds. In the scope of this invention, it has now been surprisingly found that such nonpolar, lipophilic agents can be introduced into the cellulose filaments and fibers.

It is likewise surprising that the lipophilic organic agents incorporated in the hydrophilic cellulose network can be distributed homogeneously and in microparticle form in such a way that a precisely adjustable and uniform storage as well as controlled release of these nonpolar lipophilic organic agents from the fibers is made possible.

The polymer composition according to the invention is preferably produced from a spinning solution. The agents are preferably present as micro-inclusions in the polymer composition.

Modified cellulose is understood to mean is particular carboxyethyl cellulose, methyl cellulose, nitrate cellulose, copper cellulose, viscose, i.e., cellulose xanthogenate, cellulose carbamate, and cellulose acetate.

In an alternative embodiment, the polymer is a polyamide, a polyacrylic, a polyester, or modifications thereof or a derivative thereof, and mixtures thereof. In a preferred embodiment, the polymer is a polyamide or modifications thereof. In a preferred embodiment, the polymer is a polyacrylic or modifications thereof. In a preferred embodiment, the polymer is a polyester or modifications thereof.

In a preferred embodiment, the polymer is a polyamide or a derivative thereof. In a preferred embodiment, the polymer is a polyacrylic or a derivative thereof. In a preferred embodiment, the polymer is a polyester or a derivative thereof.

Examples of polycondensation and polymerization polymers are polyamides that are substituted with methyl, hydroxy, or benzyl groups, for example. Examples of polyurethanes are those that are synthesized on the basis of polyether polyols.

In an alternative embodiment, the polymer is a polylactide or a modifications [sic] thereof or a derivatives [sic] thereof. In an alternative embodiment, the polymer is a polylactide.

The at least one agent is preferably incorporated in the polymer composition and is in particular not applied to the carrier matrix by impregnation or coating.

As it follows from the preceding description, the fibers of the thread according to the invention or of the textile surface according to the invention can have any combination of the aforementioned preferred embodiments of the polymers and of the aforementioned preferred embodiments of the aforementioned agents in particular of the petrolatum, of the fats, of the oils, of the non-saponifiable lipids, and also of the other agents.

This invention also relates to a formed body or to a plurality of formed bodies comprising a polymer composition according to the invention.

An advantage of the formed bodies according to the invention, in which the additives according to the invention are present, is the uniform incorporation of the agents in the formed body, in particular in the fiber matrix, given the different fiber cross sections that can be produced. Processing as a monofilament thread or a continuous filament thread is also possible, thus permitting a use for technical articles.

The formed bodies according to the invention can be used for the most diverse purposes.

The formed body is preferably a fiber. The fiber is preferably a staple fiber, a monofilament, a multifilament, or a continuous multifilament.

Preference is therefore given to a thread according to the invention or to a textile surface according to the invention in which the fibers are staple fibers, monofilaments, multifilaments, or continuous multifilaments.

In particular if the fiber is a cellulose fiber, if can be constructed as shown in FIGS. 1 and 2 of DE 10 2007 054 702 A1, for example. The at least one agent can be present in the form of dispersed inclusions in a matrix, in particular a cellulose matrix.

The at least one agent is preferably stabilized with at least one hydrophobic thickening agent.

In particular if a textile surface according to the invention is produced from the fibers, this textile can not only be composed of the fibers according to the invention but can also contain additional components such as cotton, lyocell, rayon, carbacell, polyester, polyamide, cellulose acetate, acrylate, polypropylene, or mixtures thereof.

This invention also relates to the use of a formed body according to the invention for producing threads.

This invention also relates to a thread containing a formed body according to the invention. This invention also relates to a thread containing the formed body according to the invention as a basic component. This invention also relates to a thread consisting of formed bodies according to the invention.

This invention also relates to a nonwoven material containing a formed body according to the invention. This invention also relates to a nonwoven material containing a thread according to the invention.

Preference is therefore given to a thread according to the invention or to a textile surface according to the invention, in which the fibers are present in the form of thread or in which the textile surface is a nonwoven material or a felt.

Preference is given to a textile surface according to the invention, in which the fibers are present in the form of thread.

The textile surface is preferably a nonwoven material or a felt. The textile surface is preferably a nonwoven material. The textile surface is preferably a felt.

Preference is therefore given to a thread according to the invention or to a textile surface according to the invention, in which the textile surface is a knitted fabric, a mesh fabric, or a woven fabric.

The textile surface is preferably a knitted fabric, a mesh fabric, or a woven fabric. The textile surface is preferably a knitted fabric. The textile surface is preferably a mesh fabric. The textile surface is preferably a woven fabric. The textile surface is preferably a knitted fabric or a mesh fabric. The textile surface is preferably a knitwear.

This invention also relates to clothing articles, sports aids, or medical aids containing a thread according to the invention or a textile surface according to the invention or containing fibers, wherein the fibers comprise a polymer composition containing a polymer and at least one agent selected from the group consisting of petrolatum, an oil, wherein the oil contains at least 25 wt % oleic acid, and mixtures thereof.

This invention also relates to clothing articles, sports aids, or medical aids containing threads, wherein the threads comprise a polymer composition Containing a polymer, petrolatum, and shea butter.

This invention also relates to clothing articles sports aids, or medical aids containing a thread according to the invention or a textile surface according to the invention or containing fibers, wherein the fibers comprise a polymer composition containing a polymer and at least one agent selected from the group consisting of petrolatum, an oil, wherein the oil contains at least 25 wt % oleic acid, a non-saponifiable lipid from an oil, wherein the oil contains at least 25 wt % oleic acid, shea butter, and mixtures thereof The invention also relates to clothing articles, sports aids, or medical aids containing a thread according to the invention or a textile surface according to the invention.

The clothing article or sports aid is preferably a jersey, sports pants, underpants, an undershirt, or a stocking. Alternatively, the clothing article can also be a glove.

The medical aid is preferably a bandage or a compression stocking. The medical aid is preferably a bandage. The medical aid is preferably a compression stocking.

This invention also relates to a clothing article or to a medical aid containing a formed body according to the invention or a thread according to the invention. These are preferably clothing articles or medical aids that are, at least partially, in direct contact with the skin when worn.

This invention also relates to a clothing article containing a formed body according to the invention or a thread according to the invention. The clothing article is preferably underwear, in particular underpants, an undershirt, or a stocking. Alternatively, the clothing article can also be a glove.

This invention also relates to a medical aid containing a formed body according to the invention or a thread according to the invention. The medical aid is preferably a compression stocking or a bandage.

This invention also relates to a sports bandage and other sports aids containing a formed body according to the invention or a thread according to the invention. This invention also relates to a sports bandage and other sports aids containing a textile surface according to the invention.

This invention also relates to the use of a polymer composition according to the invention or of a formed body according to the invention in a clothing article, in a sports aid, or in a medical aid for skin care.

This invention also relates to the use of a polymer composition according to the invention or of a formed body according to the invention in a clothing article, in a sports aid, or in a medical aid for preventing the skin from drying out.

This invention also relates to the use of fibers to produce threads or textile surfaces, in particular felts or nonwovens in which the fibers comprise a polymer composition containing a polymer and at least one agent selected from the group consisting of petrolatum, an oil, wherein the oil contains at least 25 wt % oleic acid, a non-saponifiable lipid from an oil, wherein the oil contains at least 25 wt % oleic acid, shea butter, and mixtures thereof.

This invention also relates to the use of a thread according to the invention or of a textile surface according to the invention in a clothing article, in a sports aid, or in a medical aid for skin care and/or for preventing the skin from drying out.

This invention also relates in particular to the following aspects:

Aspect 1: Polymer composition containing a polymer and at least one agent selected from the group consisting of petrolatum, an oil, wherein the oil contains at least 25 wt % oleic acid, a non-saponifiable lipid from an oil, wherein the oil contains at least 25 wt % oleic acid, shea butter, and mixtures thereof.

Aspect 2: Polymer composition containing a polymer petrolatum, and shea butter.

Aspect 3: Polymer composition containing a polymer and at least one agent selected from the group consisting of petrolatum, an oil, wherein the oil contains at least 25 wt % oleic acid, and mixture thereof.

Aspect 4: Polymer composition according to aspect 1, wherein the polymer is selected from the group consisting of cellulose, modified cellulose, polyamide, polyacrylic, polyester, polyurethane, polyethylene, polypropylene, modifications thereof, derivatives thereof, and mixtures thereof.

Aspect 5: Polymer composition according to any one of the preceding aspects, wherein the at least one agent serves as a skin penetration enhancer.

Aspect 6: Polymer composition according to any one of the preceding aspect, wherein the at least one agent is an occlusive agent.

Aspect 7: Polymer composition according to any one of the preceding aspects, wherein the at least one agent is petrolatum.

Aspect 8: Polymer composition according to any one of the preceding aspects, wherein the at least one agent is petrolatum, wherein the petrolatum contains at most 20 wt % saturated, straight chain hydrocarbons with 20 to 45 carbon atoms.

Aspect 9: Polymer composition according to any one of the preceding aspects, wherein the oil contains at least 35 wt % oleic acid, at least 20 wt % palmitic acid, at least 3 wt % palmitoleic acid, at least 5 wt % linoleic diacid, at least 5 wt % stearic diacid, and at least 0.5 wt % cis-9-octadecenoic acid.

Aspect 10: Polymer composition according to any one of the preceding aspects, wherein the oil is marula oil.

Aspect 11: Polymer composition according to any one of the preceding aspects, wherein the oil is canola oil.

Aspect 12: Polymer composition according to any one of the preceding aspects, containing petrolatum and marula oil.

Aspect 13: Polymer composition according to any one of the preceding aspects, containing petrolatum and canola oil.

Aspect 14: Shaped body comprising a polymer composition according to any one of the preceding aspects.

Aspect 15: Shaped body according to aspect 14, wherein the shaped body is a fiber.

Aspect 16: Shaped body according to aspect 15, wherein the fiber is a staple fiber, a monofilament, a multifilament, or a continuous multifilament.

Aspect 17: Use of a formed body according to any one of aspects 14 through 16 for producing threads or textile surfaces, in particular felts or nonwovens.

Aspect 18: Thread containing a formed body according to any one of aspects 14 through 16.

Aspect 19: Nonwoven material containing a formed body according to any one of aspects 14 through 16 or a thread according to aspect 18.

Aspect 20: Clothing article or medical aid containing a formed body according to any one of aspects 14 through 16 or a thread according to aspect 18.

Aspect 21: Use of a polymer compound according to any one of aspects 1 through 13 or of a formed body according to any one of aspects 14 through 16 or of a thread according to aspect 18 or of a nonwoven material according to Aspect 19 in a clothing article, in a sports aid, or in a medical aid for skin care.

The invention claimed is:

1. A thread or textile surface comprising fibers, wherein the fibers comprise a polymer composition, said polymer composition comprising a polymer; at least one agent selected from the group consisting of petrolatum, an oil or a fat, wherein the oil or the fat contains at least 25 wt % oleic acid, a non-saponifiable lipid from an oil, wherein the oil contains at least 25 wt % oleic acid, and mixtures thereof; and another agent selected from the group consisting of dicaprylyl carbonate, cetyl isononanoate, isopropyl isostearate, isostearyl isostearate, isopropyl palmitate, and mixtures thereof.

2. The thread or textile surface according to claim 1, wherein the at least one agent selected is from the group consisting of petrolatum, the oil, the non-saponifiable lipid from an oil, and mixtures thereof.

3. The thread or textile surface according to claim 1, wherein the polymer is a biopolymer.

4. The thread or textile surface according to claim 3, wherein the polymer is selected from the group consisting of cellulose, modified cellulose, viscose, polylactides, modifications thereof, derivatives thereof, and mixtures thereof.

5. The thread or textile surface according to claim 1, wherein the at least one agent is petrolatum.

6. The thread or textile surface according to claim 1, wherein the polymer composition contains petrolatum and the oil that contains at least 25 wt % oleic acid.

7. The thread or textile surface according to claim 1, wherein the oil contains at least 35 wt % oleic acid, at least 20 wt % palmitic acid, at least 3 wt % palmitoleic acid, at least 5 wt % linoleic acid, at least 5 wt % stearic acid and at least 0.5 wt % cis-9-octadecenoic acid.

8. The thread or textile surface according to claim 1, wherein the oil is manila oil, olive oil, and/or rapeseed oil.

9. The thread or textile surface according to claim 8, wherein the rapeseed oil is canola oil.

10. The thread or textile surface according to claim 1, wherein the polymer composition contains the non-saponifiable lipid.

11. The thread or textile surface according to claim 1, wherein the polymer composition contains shea butter.

12. The thread or textile surface according to claim 1, wherein the polymer composition contains petrolatum and the fat that contains at least 25 wt % oleic acid.

13. The thread or textile surface according to claim 12, wherein the polymer composition contains petrolatum and shea butter.

14. The thread or textile surface according to claim 1, wherein the at least one agent serves as a skin penetration enhancer.

15. The thread or textile surface according to claim 1, wherein the at least one agent is an occlusive agent.

16. The thread or textile surface according to claim 1, wherein the fibers are staple fibers, monofilaments, multifilaments, or continuous multifilaments.

17. The textile surface according to claim 1, wherein the fibers are present in the form of thread, or wherein the textile surface is a nonwoven material or a felt.

18. The textile surface according to claim 1, wherein the textile surface is a knitted fabric, a mesh fabric, or a woven fabric.

19. A clothing article, sports aid, or medical aid containing the thread or textile surface according to claim 1 or containing fibers, wherein the fibers comprise a polymer composition comprising a polymer; at least one agent selected from the group consisting of petrolatum, an oil or a fat, wherein the oil or the fat contains at least 25 wt % oleic acid, a non-saponifiable lipid from an oil, wherein the oil contains at least 25 wt % oleic acid, and mixtures thereof; and another agent selected from the group consisting of dicaprylyl carbonate, cetyl isononanoate, isopropyl isostearate, isostearyl isostearate, isopropyl palmitate, and mixtures thereof.

20. The clothing article or sports aid according to claim 19, wherein the clothing article or sports aid is a jersey, sports pants, underpants, an undershirt, or a stocking.

21. The medical aid according to claim 19, wherein the medical aid is a bandage or a compression stocking.

22. The thread or textile surface of claim 1, wherein the at least one agent and the another agent are present as micro-inclusions in the polymer composition.

* * * * *